(12) United States Patent
Rudolph et al.

(10) Patent No.: US 7,064,216 B2
(45) Date of Patent: Jun. 20, 2006

(54) CONDENSATION REAGENTS AND A PROCESS FOR THEIR PREPARATION

(75) Inventors: Joachim Rudolph, Guilford, CT (US); Ralf Wischnat, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/029,642

(22) Filed: Dec. 18, 2001

(65) Prior Publication Data

US 2002/0156287 A1 Oct. 24, 2002

(30) Foreign Application Priority Data

Jul. 2, 2001 (DE) .......................... 101 31 572
Dec. 20, 2001 (DE) .......................... 100 63 495

(51) Int. Cl.
*C07D 277/20* (2006.01)
*C07D 277/62* (2006.01)

(52) U.S. Cl. ........................ 548/152; 548/202
(58) Field of Classification Search ................. 548/152
See application file for complete search history.

(56) References Cited

U.S. PATENT DOCUMENTS 2,916,487 A * 12/1959 de Stevens ................. 546/176

FOREIGN PATENT DOCUMENTS

| JP | 44032406 | 12/1969 |
|---|---|---|
| WO | 97/48687 | 12/1997 |

OTHER PUBLICATIONS

Tetrahedron Letters, 40, (month unavailable) 1999, pp. 8301–8304, Peng Li and Jie Cheng Xu, "A novel thiazolium type peptide coupling reagent for hindered amino acids".
Journal of Organometallic Chemistry, 544, (month unavailable) 1997, pp. 91–100, Helgard G. Raubenheimer, Pierre J. Olivier, Louise Lindeque, Mieke Desmet Jan Hrušak and Gert J. Kruger, "Oxidative additional of mono and bis–(carbene) complexes derived from imidazolyl and thiazolyl gold(I) compounds".
Dalton Trans, month unavailable 7, (month unavailable) 1974, pp. 760–764, Paul J. Fraser, Warren R. Roper and F. Gordon A. Stone, "Carbene Complexes of Iridium, Rhodium, Manganese, Chromium, and Iron containing Thiazolidinylidene and Pyridinylidene Ligands".
Chemical Abstracts 55:10471, pp. 1795–1797, Hitoshi Minato: "Synthesis of 2–Bromo–4–methylthiazole. On the Application of Genapathi's Method", 1961.
Zh Obshch. Khim., (month unavailable) English translation in J. Gen. Chem. USSR, pp. 799–803, B.M. Mikhailov and V.P. Bronovitskaya, Bromination of Thiazole Derivatives with N–Bromosuccinimide, Year Not Available.
Current Sci. (India) Sep. 9, 1952, K. Granapathi, K.D. Kulkami, "Orientation in the Thiazole Nucleus", p. 314–315.
J. Sci Industr. Res. vol. 21B, Jun. 1962, pp. 291–292, J.S. Bhalla, N.K. Ralhan and K.S. Narang, "Synthesis of Some 2–Bromothiazoles".
Synthetic Communications, 28(8), (month unavailable) 1998, pp. 1451–1462, Joachim G. Schanti, and Irene M. Lagoja, "Expedient Synthesis of N–Substituted 2–Aminothiazoles".
Indian J. Chem., vol. 30B, Dec. 1991, pp. 1152–1155, R.P. Kapoor, (Km) V.P. Sharma, Om V. Singh and C.P. Garg, "Synthesis of 3–(2–N–substituted aminothiazol–4–yl)–2–methyl–chromones and 6–(2–N–substituted aminothiazol–4–yl)–2,3–dimethylchromones as potential CNS agents".
J. Org. Chem., (month unavailable) 1986, 51, pp. 543–545, Ashot Merijanian, Gurdial M. Sharma, John Moushati and Karl Gunderson, "Steric Effects or Ortho Substituents on Acid–Catalyzed Cyclization of Thiocyanatoacetophenones".
J. Indian Chem. vol. 32, No. 7, (month unavailable) 1955, D.S. Bariana, H.S. Sachdev and K.S. Narang, "Studies in Thiazoles. Part I" pp. 427–430.
J. Am. Chem. So. 74, Apr. 5, 1952, pp. 1719–1720, James T. Gregory and Roger A. Mathes, "Reactions of 3–Thiocyano–2–butanone. I. The Preparation of 2–Substituted–4,5–dimethylthiazoles".
Indian J. Chem., vol. 5, Oct. 1967, p. 526.
Zh. Obshch. Khim, 29, (month unavailable) 1959, pp. 2619–2621 of the English edition, pp. 2619–2622, A.I. Gurevich, "Complexes of Sulfonamides with Amines".
Tetrahedron, vol. 15, (month unavailable) 1961, pp. 53–59, G.M. Sharma, H.S. Sachdev, N.K. Ralhan, H. Singh, G. Sarjit Sandhu, K. Gandhi nd K.S. Narang, "Thiopegan Derivatives–XXI".

(Continued)

*Primary Examiner*—Laura L. Stockton
(74) *Attorney, Agent, or Firm*—Didercio van Eyl (57) ABSTRACT

The present invention relates to new bromo- and chlorothiazolium salts of the formula (I)

$$\underset{R^1}{\overset{R^3}{\underset{R^2}{\bigwedge}}}\overset{S}{\underset{N^+}{\bigvee}}R^4\ X^-\quad (I)$$

in which
$R^1$, $R^2$, $R^3$, $R^4$, n and $X^-$ have the meaning indicated in the disclosure, a process for their preparation, their use as condensation reagents, particularly as peptide coupling reagents, and intermediates for the preparation of these compounds.

5 Claims, 1 Drawing Sheet

OTHER PUBLICATIONS

Jour. Indian Chem. Soc., vol. 31, No. 11, (month unavailable) 848–852, D.S. Bariana, M.S. Dhatt, H.S. Sachdev and K.S. Narang, "Thiopegan Derivatives. Part V", 1954.

Chemical Abstracts, vol. 55, No. 13, Jun. 6, 1961 Columbus, Ohio, US; abstract No. 12388f, Ralhan N.K. et al: "Thiazoles. IV. Preparation of some 2–bromothiazoles" XP002201066 Zusammenfassung & J. Indian Chem. Soc., Bd. 37, 1960, Seiten 773–774.

Chemical Abstract, vol. 52, No. 7, Apr. 10, 1958 Columbus, Ohio, US; abstract No. 5383d, Sharma G.M. et al: Thaizoles. II Synthesis of some 2–chloro– and 2–hydroxythiazoles' XP002201068 Zusammenfassung & J. Sci. Ind. Research (India) Bd. 16B, 1957, Seiten 411–413.

Dhami K.S. et al: "Studies in Thiaoles. v. Synthesis of some 2–chloro– and 2–hydroxythiazoles" Journal of Organic Chemistry, Bd. 27, Nr. 6, Jun. 1962, Seiten 2147–2149, XP002201063 das ganzes Dokument.

Database Crossfire Beilstein 'Online! Beilstein Institut zur Föderung der Chemischen Wissenchaften, Frankfurt am Main, DE; Database accession No. Reaction ID 1255281 XP002201069 Zusammenfassung & Indian J. Chem Bd. 10, 1972, Seiten 605–607.

Li P. et al: Total synthesis of cyclosporin O both in solution and in the solid phase using novel Thiazolum–, immonium–, and pyridinium–type coupling reagents: BEMT, BDMP, and BEP' Journal of Organic Chemistry, BD. 65, Nr. 10, May 19, 2000, kSeiten 2951–2958, XP002191973, das ganze Dokument Sugimoto H. et al: "Activation of dithiocarbamate by 2–halothiazolium salts" Journal of Organic Chemistry, Bd. 53, Nr. 10, Mai 1988 (May 13, 1988), Seiten 2263–2267, XP002191974 das ganze Dokument, insebesondere Verbindingen 2c and 2d.

Destevens G. et al: "Investigations in heterocycles. I. Cycloalken[d]thiazolin–2–ones and their Analgetic properties" Journal of the American Chemical Society, Bd. 79, Nr. 19, Oct. 5, 1957, Seiten 5263–5270, XP002191976, das ganze Dokument, insbesondere Seite 5264, Schema I, sowie Seite 5268, rechte Spalte, zweiter Textabschnitt.

Chemical Abstracts, vol. 133, No. 20, Nov. 12, 2000 Columbus, Ohio, US; Abstract No. 2820835, Seite 800; XP002191977 Zusammenfassung & Database Caplus 'Online! Chemical Abstracts Service, Columbus Ohio, US.

Database accession No. 2000:749442 XP002191978 RN 299219–84–4, 255897–31–5 and 299218–66–9 & CN 1 243 828 A (Faming Zhuanli Shenqing Gongkai Shuomingshu) Feb. 9, 2000.

CAS No. 26847–01–8, Year Not Available.

CAS No. 667–86–7, Year Not Available.

* cited by examiner

FIG. 1

CONDENSATION REAGENTS AND A PROCESS FOR THEIR PREPARATION

BACKGROUND OF THE INVENTION

The present invention relates to new bromothiazolium salts and chlorothiazolium salts and their use as condensation reagents, particularly as peptide coupling reagents, a process for their preparation, and intermediates needed in this process.

For the preparation of efficient peptide coupling reagents such as, for example, of the peptide coupling reagent 2-bromo-3-ethyl-4-methyl-thiazolium tetrafluoroborate (BEMT, see Tetrahedron Lett. 1999, 40, 8301–8304), published for the first time in 1999 by P. Li, bromothiazoles such as, for example, 2-bromo-4-methylthiazole are needed as immediate precursors. The processes known for the preparation of these compounds, particularly of 2-bromo-4-methylthiazole, are not satisfactory and are unsuitable for preparation on a molar or larger scale. The structurally similar, but less active reagent 2-bromo-1-ethyl-pyridinium tetrafluoroborate (BEP, see Chem. Lett. 2000, 204–205) is, for example, significantly easier to prepare, longer known, and commercially obtainable. There is therefore a need for improved processes for the preparation of peptide coupling reagents such as BEMT and suitable bromothiazoles such as 2-bromo-4-methylthiazole and routes for their preparation.

There is likewise a need for further peptide coupling reagents that are employed with higher efficiency and can be prepared using practicable processes. Thus, for example, the 2-chlorothiazole derivative of BEMT, 2-chloro-3-ethyl-4-methylthiazole tetrafluoroborate (CEMT, CAS No. 667-86-7, Dalton Trans. (1974), 7, 760–764) and its precursor, 2-chloromethylthiazole (CMT, CAS No. 26847-01-8, JP 44/32,406) are known compounds. However, while BEMT has already been described as a coupling reagent, the chloro derivative (CEMT) has hitherto not been disclosed as a coupling reagent. The key structural unit for the preparation of CEMT, CMT has moreover always been prepared by means of a process route which, like the processes for the preparation of BEMT, has disadvantages (Raubenheimer, H. G. et al (1997), Organomet. Chem. 544, 91–100).

2-Bromo-4-methylthiazole can be prepared from 2-amino-4-methylthiazole by Sandmeyer reaction. The work-up is complicated and the yield of 32% of theory is unsatisfactory (cf. Yakugaku Zasshi 1960, 80, 1795 cited in C.A. 55:10417). Li, in 1999 (cf. above), only indicates a yield for the overall synthesis sequence for the preparation of BEMT that is not very satisfactory. In our own attempts to adjust this, it was additionally found that approximately 30% of 2,5-dibromo-4-methylthiazole is formed as an undesired and poorly separable by-product. A further synthesis route described is the bromination of 4-methylthiazole. The reaction with N-bromosuccinimide in tetrachloromethane has further disadvantages above and beyond the low yield of only 26% (cf. Zh. Obshch. Khim. 1957, 27, 726 English translation in J. Gen. Chem. USSR, p. 799). On the one hand, the reagent is very expensive when used industrially and, on the other hand, the use of tetrachloromethane is undesirable for industrial safety reasons and even prohibited in some countries. Bromination with elemental bromine has hitherto not been successful (cf. Current Sci. (India), 1952, 21, 314 cited in C.A. 48:2046 and Zh. Obshch. Khim.).

The synthesis of 2-bromo-4-ethylthiazole and 2-bromo-4,5-dimethylthiazole by cyclization of -thiocyanatoalkanones with hydrobromic acid is known from J. Sci. Ind. Res. Sect. B 1962, 21, 291. Nothing has been published hitherto about an analogous synthesis of 2-bromo-4-methylthiazole, despite the existing need.

SUMMARY OF THE INVENTION

There have now been found new bromo- and chlorothiazolium salts of the formula (I)

(I)

in which $R^1$ represents methyl, ethyl, n-propyl, isopropyl, hydroxyl, methylsulfonyl, ethylsulfonyl, phenylsulfonyl, p-methylphenylsulfonyl, or benzyl that is optionally substituted by halogen, nitro, $C_1$–$C_4$-alkyl, or $C_1$–$C_4$-alkoxy, $R^2$ represents $C_1$–$C_4$-alkyl, hydroxyl, methylsulfonyl, ethylsulfonyl, phenylsulfonyl, p-methylphenylsulfonyl, phenyl that is optionally substituted by halogen, $NO_2$, $C_1$–$C_4$-alkyl, $C_1$–$C_4$-halogenoalkyl, $C_1$–$C_4$-alkylsulfonyl, $C_1$–$C_4$-alkoxy, $C_1$–$C_4$-halogenoalkoxy, $C_1$–$C_4$-alkoxycarbonyl, $C_1$–$C_4$-halogenoalkoxycarbonyl, $C_1$–$C_4$-alkyl-carbonyloxy, or $C_1$–$C_4$-halogenoalkylcarbonyloxy, benzyl that is optionally substituted by halogen, nitro, $C_1$–$C_4$-alkyl, or $C_1$–$C_4$-alkoxy, or pyrrolyl, thienyl, naphthyl, or benzothiophenyl, each of which is optionally substituted by halogen, $C_1$–$C_4$-alkyl, or $C_1$–$C_4$-halogenoalkyl, $R^3$ represents hydrogen, methyl, or ethyl, or $R^2$ and $R^3$ together represent —$(CH_2)_n$— that is optionally substituted by halogen, $NO_2$, carboxyl, carbonyl, $C_1$–$C_4$-alkyl, $C_1$–$C_4$-halogenoalkyl, $C_1$–$C_4$-alkoxy, or $C_1$–$C_4$-halogenoalkoxy or the optionally halogen-, $NO_2$—, $C_1$–$C_4$-alkyl-, $C_1$–$C_4$-halogenoalkyl-, $C_1$–$C_4$-alkoxy-, or $C_1$–$C_4$-halogenoalkoxy-substituted groups having the formulas where the arrows mark the points of linkage to the thiazolium ring, and n represents 3, 4 or 5, $R^4$ represents bromine or chlorine, and $X^-$ represents chloride, bromide, iodide, hydrogen sulfate, ½ equivalent of sulfate, sulfate, hexachloroantimonate ($SbCl_6^-$), methane-sulfonate (mesylate), trifluoromethanesulfonate (triflate), p-toluene-sulfonate (tosylate), tetrafluoroborate, tetraphenylborate, or hexafluorophosphate, excluding the compounds 2-bromo-3-ethyl-4-methylthiazolium tetrafluoroborate and 2-bromo-3-ethyl-4- methylthiazolium hexachloroantimonate, 2-chloro-3-ethyl-4-methylthiazolium tetrafluoroborate and 2-chloro-3-ethyl-4-methylthiazolium hexachloroantimonate, 2-bromo-3-methyl-4-phenylthiazolium tetrafluoroborate, 2-chloro-3-ethyl-4,5-dimethylthiazolium tetrafluoroborate, and 2-chloro-3,4-dimethylthiazolium tetrafluoroborate.

DETAILED DESCRIPTION OF THE INVENTION

Preferred substituents or preferred ranges of the radicals present in the formulas mentioned above and below are defined below.

$R^1$ preferably represents methyl, ethyl, n-propyl, hydroxyl, methylsulfonyl, ethylsulfonyl, or benzyl that is optionally substituted by fluorine and/or chlorine, methyl, ethyl, n- or i-propyl, trifluoromethyl, methoxy, ethoxy, or n- or i-propoxy.

$R^2$ preferably represents methyl, ethyl, n-propyl, isopropyl, n-butyl, sec-butyl, isobutyl, or benzyl or phenyl that is optionally substituted by fluorine and/or chlorine, methyl, ethyl, n- or i-propyl, methoxy, ethoxy or n- or i-propoxy.

$R^3$ preferably represents hydrogen or methyl.

$R^2$ and $R^3$ preferably also together represent $-(CH_2)_n-$ substituted by fluorine and/or chlorine, methyl, ethyl, trifluoromethyl, methoxy, ethoxy, or carbonyl or groups having the formulas where the arrows mark the points of linkage to the thiazolium ring.

n preferably represents 3 or 4.

$R^4$ preferably represents bromine.

$X^-$ preferably represents bromide, ½ equivalent of sulfate, sulfate, $SbCl_6^-$, mesylate, triflate, tosylate, tetrafluoroborate, tetraphenyl-borate, or hexafluorophosphate.

$R^1$ preferably represents methyl, ethyl, methylsulfonyl, ethylsulfonyl or benzyl that is optionally substituted by fluorine and/or chlorine.

$R^2$ particularly preferably represents methyl, ethyl, n-propyl, n-butyl or phenyl that is optionally substituted by fluorine and/or chlorine, methyl, or ethyl.

$R^3$ particularly preferably represents hydrogen.

$R^2$ and $R^3$ particularly preferably also together represent $-(CH_2)_n-$ that is optionally substituted by fluorine and/or chlorine, methyl, ethyl, or carbonyl.

$X^-$ particularly preferably represents bromide, ½ equivalent of sulfate, sulfate, or tetrafluoroborate.

$R^1$ very particularly preferably represents methyl, ethyl, n-propyl, or isopropyl.

$R^2$ very particularly preferably represents methyl or ethyl.

$X^-$ very particularly preferably represents tetrafluoroborate.

Independently thereof, those compounds are also preferred in which $R^2$ represents isobutyl or ethyl or n-propyl and $R^3$ represents isopropyl or methyl or ethyl.

A particularly preferred group of compounds of the formula (I) are those compounds in which $R^4$ represents bromine.

The compounds of the formula (I) are particularly suitable as condensation reagents, particularly in peptide synthesis as peptide coupling reagents.

According to the invention, preferred compounds of the formula (I) are those in which a combination of the meanings mentioned above as preferred is present.

According to the invention, particularly preferred compounds of the formula (I) are those in which a combination of the meanings mentioned above as particularly preferred is present.

According to the invention, very particularly preferred compounds of the formula (I) are those in which a combination of the meanings mentioned above as very particularly preferred is present.

The above-mentioned general definitions of radicals or explanations or definitions of radicals or explanations mentioned in preferred ranges can be combined with one another in any desired manner, i.e., also between the particular ranges and preferred ranges. These definitions apply correspondingly to the final product and to the precursors and intermediates.

The new bromo- and chlorothiazolium salts of the formula (I) are particularly suitable for use as condensation reagents, particularly as peptide coupling reagents. In particular, the bromo- and chlorothiazolium salts of the formula (I-2) mentioned below are suitable as condensation reagents, particularly as peptide coupling reagents. Furthermore, the new bromo- and chlorothiazolium salts of the formula (I), particularly those of the formula (I-2), are suitable as condensation reagents for the formation of an amide bond between a carboxylic acid or a carboxylic acid derivative and an amine.

The new bromo- and chlorothiazolium salts of the formula (I) or of the formulas (I-1) and (I-2) described below are obtained by the processes (A) and (B) described below.

(A) The new bromo- and chlorothiazolium salts of the formula (I-1)

(I-1)

in which $R^1$, $R^2$, $R^3$ and $R^4$ have one of the meanings indicated above, and $X'^-$ represents chloride, bromide, iodide, hydrogen sulfate, ½ equivalent of sulfate, sulfate, $SbCl_6^-$, methanesulfonate, trifluoromethanesulfonate, or p-toluenesulfonate, are obtained when bromo- and chlorothiazoles of the formula (II)

(II)

in which

$R^2$, $R^3$ and $R^4$ have the meaning indicated above, (a) are reacted with alkylating reagents of the formula (III)

(III), in which
$R^1$ has the meaning indicated above, and
X' represents chlorine, bromine, iodine, sulfoxy, ½ equivalent of sulfate, sulfate, $SbCl_6^-$, methylsulfonyloxy, trifluorosulfonyloxy, or toluenesulfonyloxy, in the presence of a diluent, or

(b) are reacted with sulfonating reagents of the formula (VII)

(VII)

in which
$R^1$ has the meaning indicated above and preferably represents, for example, methyl, ethyl, phenyl, or 4-methylphenyl,
in the presence of a diluent, the reaction preferably being carried out in the presence of a base such as, for example, a tertiary amine (e.g., triethylamine) or pyridine, or (c) are oxidized using hydrogen peroxide ($H_2O_2$), peracids, or NaOCl.

(B) The new bromo- and chlorothiazolium salts of the formula (I-2)

(I-2)

in which
$R^1$, $R^2$, $R^3$ and $R^4$ have the meaning indicated above, and
$X'''^-$ represents tetrafluoroborate, tetraphenylborate, or hexafluorophosphate,
are obtained when
(a) bromo- and chlorothiazoles of the formula (II)

(II)

in which
$R^2$, $R^3$ and $R^4$ have the meaning indicated above, are reacted with alkylating reagents of the formula (IV)

(IV), in which
$R^1$ and $X'''^-$ have the meaning indicated above, in the presence of a diluent, or when

(b) compounds of the formula (I-1)

(I-1)

in which
$R^1$, $R^2$, $R^3$, $R^4$ and $X'^-$ have the meaning indicated above, are employed and the anion $X'^-$ is exchanged with tetrafluoroboric acid, tetraphenylboric acid, or hexafluoro-phosphoric acid or an anion exchanger loaded with these acids for an anion having the meaning of $X'''^-$ indicated above.

The compounds of the formula (II) are not yet known from the literature, with the exception of compounds in which $R^4$ represents bromine and $R^2$ represents $CH_3$ when $R^3$ represents hydrogen or $CH_3$; in which $R^4$ represents chlorine and $R^2$ represents $CH_3$ when $R^3$ represents hydrogen; and in which $R^4$ represents bromine and $R^2$ represents ethyl when $R^3$ represents hydrogen. The new compounds are likewise a subject of the present invention.

The compounds of the formula (II) are obtained when compounds of the formula (V)

(V)

in which
$R^2$ and $R^3$ have one of the meanings indicated above, are reacted with hydrogen bromide or hydrogen chloride in the presence of a diluent and the hydrogen bromide or hydrogen chloride is then released from the compound of the formula (VI) first obtained (VI)

in which $R^2$, $R^3$ and $R^4$ have one of the meanings indicated for formula (II) and $R^{4-}$ is bromide or chloride.

The bromo- and chlorothiazoles of the formula (II-1)

(II-1)

in which
n represents 1 or 2
are likewise not yet known from the literature and are likewise in particular a subject of this invention.

Thus the bromo- and chlorothiazoles of the formula (II-1) are obtained when, as generally described at the beginning, 2-thiocyanatocyclopentanone or

2-thiocyanatocyclohexanone is reacted with hydrogen bromide or hydrogen chloride in the presence of a diluent and the hydrogen bromide or hydrogen chloride is then released from the hydrobromide or hydrochloride first obtained.

The compounds of the formula (V) are known and/or can be prepared by known processes (see, for example, Schantl et al. 1998, Synth. Commun. 28,1451–1462, Indian J. Chem., Sect. B (1991), 30, 1152–1155, J. Org. Chem. (1986), 51, 543–545, J. Indian Chem. Soc. (1965), 32, 427, J. Am. Chem. Soc. (1952), 74,1719, Indian J. Chem. (1967), 5, 526).

Thus the compound 2-chloro-4-methylthiazole as in formula (II), which is known from the literature, is obtained when 1-thiocyanato-2-propanone is reacted with hydrogen chloride in the presence of a diluent and the hydrogen chloride is then released from the 2-chloro-4-methylthiazolium chloride first obtained. This process is fully included by the present invention. This process can be represented as follows as an example of the preparation of compounds of the formula (II):

Thus the compound 2-bromo-4-methylthiazole as in formula (II), which is known from the literature, is further obtained when 1-thiocyanato-2-propanone is reacted with hydrogen bromide in the presence of a diluent and the hydrogen bromide is then released from the 2-bromo-4-methylthiazolium bromide first obtained. This process is fully included by the present invention. This process can be represented as follows as an example of the preparation of compounds of the formula (II):

It is advantageous in this case that this synthesis takes place in high yield from a very readily accessible starting material. 1-Thiocyanato-2-propanone is obtainable in two reaction steps by chlorination, bromination, or iodination of acetone and subsequent reaction with thiocyanates (cf., for example, Chem. Ber. 1928, 61, 1784).

Using the process according to the invention, access to 2-bromo-4-methylthiazole as a valuable intermediate has been significantly improved. This is all the more surprising, as this has obviously not been successfully carried out in the almost 40 years since the publication of the synthesis of the 4-ethyl compound. Whereas 2-bromo-4-methylthiazole was already employed as an active compound precursor in two Swiss patents (CH 210790; CH 210784) applied for by Ciba in 1938, the poor accessibility stood in the way of wide use until today. This object of providing a better process is achieved by the invention described here.

The preparation of the compound 2-bromo-3-ethyl-4-methylthiazolium tetrafluoroborate as in formula (I), which is already known from the literature, is carried out, for example, by first reacting 1-thiocyanato-2-propanone as in the process according to the invention described above to give 2-bromo-4-methylthiazole and, in a further step, reacting this with triethyloxonium tetrafluoroborate. The process can be represented as follows:

This process is fully included by the present invention.

The preparation of the compound 2-chloro-3-ethyl-4-methyl-thiazolium tetrafluoroborate as in formula (I), which is already known from the literature, is carried out as in the process according to the invention by reacting 1-thiocyanato-2-propanone to give 2-chloro-4-methylthiazole and, in a further step, reacting this with triethyloxonium tetrafluoroborate. The process can be represented as follows (see also the preparation examples):

This process is fully included by the present invention.

The cyclization according to the invention of compounds of the formula (V) with hydrogen bromide or hydrogen chloride is carried out in the presence of a diluent. Certain aprotic organic solvents and any desired mixtures thereof are suitable for this. Examples that may be mentioned are alicyclic or aromatic hydrocarbons, such as, for example, petroleum ether, hexane, heptane, cyclohexane, methylcyclohexane, benzene, toluene, xylene, or decalin; halogenated hydrocarbons, such as, for example, chlorobenzene, dichlorobenzene, methylene chloride, chloroform, tetra-chloromethane, dichloroethane, trichloroethane, or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxy-ethane, diethylene glycol dimethyl ether, or anisole. Methylene chloride, chloroform, 1,2-dichloroethane, diethyl ether, or tert-butyl methyl ether, particularly preferably methylene chloride, are preferably employed.

2.0 to 10 mol (preferably 2.1 to 7 mol) of hydrogen bromide or hydrogen chloride and 0.5 to 5 liter (preferably 1 to 3 liter) of diluent are employed in the cyclization per mole of the compound of the formula (V).

The cyclization is carried out with exclusion of moisture. This can be guaranteed, for example, by employing commercially available dry diluents or rendering these absolute according to the generally customary drying methods, as well as by employing dry hydrogen bromide or hydrogen chloride and/or passing these through a deep-frozen gas trap and/or a drying tower containing a suitable drying agent or a gas scrubbing device, such as, for example, a wash bottle containing concentrated sulfuric acid. The cyclization is expediently carried out such that the compound of the formula (V) is preferably introduced into the diluent and the hydrogen bromide or hydrogen chloride is then passed in with temperature control and good dispersion. The exothermic reaction is in general carried out at a temperature of −30 to +40° C., preferably at −15 to +30° C. It is particularly advantageous to keep the temperature during the introduction of hydrogen bromide or hydrogen chloride between 0 and +10° C. and then to after-react for a further ½ to 15 hours at room temperature and allow to crystallize. The compound of the formula (VI) resulting therefrom can conveniently be obtained by a solid/liquid separation process, such as, for example, filtration or centrifugation.

For the release of the bromo- and chlorothiazoles of the formula (II) from the hydrobromide or the hydrochloride, weaker acid acceptors are suitable. Those possible are organic and inorganic bases. These weaker acid acceptors preferably include alkali metal carbonates or hydrogen carbonates, such as, for example, sodium, potassium, or ammonium carbonate, sodium hydrogen- or potassium hydrogen carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN), or diazabicycloundecene. Sodium hydrogen carbonate and potassium hydrogen carbonate are preferred.

The release of the bromo- and chlorothiazoles as in formula (II) from the hydrobromide or hydrochloride can be carried out without a prior drying step in the same diluent as the cyclization. For this, it is advantageous when separating off the hydrobromide or hydrochloride to wash with some diluent in order largely to remove the excess hydrogen bromide or hydrogen chloride. The bromothiazolium bromide or chlorothiazolium chloride is suspended in the diluent (in general 0.8 to 3 liter per mole of hydrobromide or hydrochloride) and the base is then added. Preferably, an aqueous solution of an inorganic base is employed, such as, for example, sodium hydrogen carbonate solution. The concentration is not critical here. Preferably, more highly concentrated to saturated solutions are taken. Per mole of hydrobromide or hydrochloride, 1.0 to 1.5 equivalents (preferably 1.0 to 1.2 equivalents) of base are employed. The neutralization is in general carried out at a temperature from −20 to +30° C., preferably at −5 to +10° C.

The bromo- or chlorothiazole is isolated according to the customary methods of organic chemistry. Preferably, a phase separation is carried out and the organic phase is distilled. Before the distillation, drying can be carried out using a drying agent such as, for example, magnesium or sodium sulfate, calcium chloride, silica gel, or molecular sieve.

The reagents of the formula (III), (VII), and (IV) needed for the preparation according to the invention of the 3-alkyl-2-halogenothiazolium salts of the formulas (I-1) or (I-2) by alkylation are generally known or commercially obtainable.

The preparation according to the invention of the 3-alkyl-2-halogenothiazolium salts of the formula (I-1) or formula (I-2) is in each case carried out in the presence of a diluent. Certain aprotic organic solvents and any desired mixtures thereof are suitable for this. Examples that may be mentioned are alicyclic or aromatic hydrocarbons, such as, for example, petroleum ether, hexane, heptane, cyclohexane, methylcyclohexane, benzene, toluene, xylene, or decalin; halogenated hydrocarbons, such as, for example, chlorobenzene, dichlorobenzene, methylene chloride, chloroform, tetrachloromethane, dichloroethane, trichloroethane, or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether, or anisole, methyl cyanide, acetone, dimethylformamide, ethyl acetate, or homologs, and dimethyl sulfate, which can simultaneously be used as an alkylating agent.

In general, 0.8 to 2 (preferably 1.0 to 1.5) equivalents of alkylating reagent of the formula (III) or (IV) and 0.1 to 5 liter of diluent are employed per mole of 2-bromo- or chlorothiazole of the formula (II).

In the process as in (A)(b) for the preparation of compounds of the formula (I-1), hydrocarbons, ethers, and halogenohydrocarbons are particularly suitable as diluents. Polar protic solvents such as DMF are also possible, likewise mixtures of the solvents mentioned above. In this process route, all reagents are preferably employed in molar ratios or alternatively in excesses. Preferably, this process is carried out at temperatures from −20° C. to +100° C. (see also Zh. Obshch. Khim. (1959), 29, 2655–2657, Engl. ed. p. 2619–2621; Organikum, VEB Deutscher Verlag der Wissenschaften Berlin (1988), 597–615).

Compounds of the formula (I) in which $R^1$ is carbonyl are accessible as in process (A)(c) by oxidation of compounds of the formula (II) with hydrogen peroxide, peracids, or NaOCl (see, for example, Organikum, VEB Deutscher Verlag der Wissenschaften Berlin (1988), 597–615).

The alkylation is carried out under generally customary conditions. The reaction is carried out, for example, at a temperature from −80 to +100° C. The preferred temperature depends on the reactivity of the reagent, which is different in each case.

The reaction of 2-bromo-4-methylthiazole to give BEMT or of 2-chloro-4-methylthiazole to give CEMT is carried out in the presence of a diluent. Certain aprotic organic solvents and any desired mixtures thereof are suitable for this. Examples that may be mentioned are the same solvents which are listed in the case of the cyclization. Methylene chloride is preferably employed.

The triethyloxonium tetrafluoroborate needed for carrying out this reaction is commercially obtainable. Approximately equimolar amounts of 2-bromo-4-methylthiazole or 2-chloro-4-methylthiazole and triethyloxonium tetrafluoroborate and 0.5 to 2 liter of diluent per mole batch size are employed. The reaction is expediently carried out such that the 2-bromo-4-methylthiazole or 2-chloro-4-methylthiazole is preferably introduced into the diluent and the triethyloxonium tetrafluoroborate is then metered in. The reaction is in general carried out at 0 to +60° C., preferably at 15 to 55° C. It is particularly advantageous to keep the temperature during the addition between 20 and +30° C. and then to heat the mixture, for example, to about 50° C. and to allow it to after-react for ½ to 2 hours.

The work-up is carried out according to generally known methods of organic chemistry. A preferred work-up after reaction in dichloromethane is crystallization by addition of only slightly polar aprotic diluents such as, for example, tert-butyl methyl ether, diethyl ether, or hexane. If desired, the 2-bromo-3-ethyl-4-methylthiazolium tetrafluoroborate or the 2-chloro-3-ethyl-4-methyl-thiazolium tetrafluoroborate can be further purified in good yield by crystallization from alcohols such as, for example, methanol, ethanol, or isopropanol or other organic solvents.

The reactions of the processes according to the invention can be carried out at normal pressure or at elevated pressure. Preferably, the reaction is carried out at normal pressure. If not stated otherwise, the reaction is carried out and worked up and the reaction products are isolated according to generally customary, known methods.

The following examples further illustrate details for the preparation and use of the compounds of this invention. The invention, which is set forth in the foregoing disclosure, is not to be limited either in spirit or scope by these examples. Those skilled in the art will readily understand that known variations of the conditions and processes of the following preparative procedures can be used to prepare these compounds. Unless otherwise noted, all temperatures are degrees Celsius and all percentages are percentages by weight.

EXAMPLES

Preparation Examples

Example 1

110 g (0.60 mol) of 2-bromo-4-methylthiazole were added at room temperature to a solution of 117 g (0.58 mol) of triethyloxonium tetrafluoroborate in 400 ml of dichloromethane such that a temperature of 30° C. was not exceeded. After addition was complete, the mixture was warmed to 50° C. for 60 min and then cooled to room temperature. For complete crystallization, the reaction mixture was treated with 300 ml of methyl tert-butyl ether, the crystals were filtered off with suction, and the product was then recrystallized from isopropanol.

Yield of 2-bromo-3-ethyl-4-methylthiazolium tetrafluoroborate (BEMT): 140 g (80%), white crystals. M.p.: 184° C. $^1$H-NMR (400 MHz, DMSO-$d_6$): δ=1.45 (t, J=7.3 Hz, 3H, CH$_2$CH$_3$), 2.62 (s, 3H, CH$_3$ thiazole), 3.95 (q, J=7.3 Hz, 2H, CH$_2$CH$_3$), 8.05 (s,1H, thiazole). $^{13}$C-NMR (400 MHz, CH$_3$CN-$d_3$): δ=13.9, 14.7, 50.0, 148.5, 123.4, 145.4. MS (ESI$^+$): m/z=206 ($^{79}$Br), 208 ($^{81}$Br).

Example 2a 1.50 g (8.42 mmol) of 2-bromo-4-methylthiazole were added at room temperature to a solution of 1.25 g (8.42 mmol) of trimethyloxonium tetrafluoroborate in 5 ml of dichloroethane. After addition was complete, the mixture was warmed to 50° C. for 30 min and then cooled to room temperature. For complete crystallization, the reaction mixture was treated with about 20 ml of methyl tert-butyl ether and the crystals were filtered off with suction.

Yield of 2-bromo-3-methyl-4-methylthiazole tetrafluoroborate: 2.3 g (99%), white crystals M.p.: 184° C. $^1$H-NMR (400 MHz, DMSO-$d_6$): δ=2.56 (s, 3H, CH$_3$ thiazole), 3.96 (s, 3H, CH$_3$), 8.03 (s, 1H, thiazole). $^{13}$C-NMR (400 MHz, CH$_3$CN-$d_3$): δ=14.0, 39.3, 120.8, 144.8, 147.7. MS (ESI$^+$): m/z=192 ($^{79}$Br), 194 ($^{81}$Br).

Example 2b 5.33 g (56.2 mmol) of bromomethane were added in a pressure vessel at 25° C. to a solution of 1.0 g (5.62 mmol) of 2-bromo-4-methylthiazole in 4.0 ml of N,N-dimethylformamide. The vessel was closed and warmed to 60° C. After stirring for 12 h, the mixture was cooled to 25° C., the solvent was removed in vacuo and the residue was codistilled three times with ethyl acetate to remove the last traces of DMF. The residue was recrystallized from isopropanol.

Yield of 2-bromo-3-methyl-4-methylthiazole tetrafluoroborate: 0.47 g (31%), white crystals M.p.: 260° C. (decomposition). $^1$H-NMR (400 MHz, MeOH-$d_3$): δ=2.63 (s, 3H, CH$_3$thiazole), 4.08 (s, 3H, CH$_3$), 7.98 (s,1H, thiazole). $^{13}$C-NMR (400 MHz, MeOH-$d_3$): δ=15.2, 40.4, 122.5, 147.6, 149.3. MS (ESI$^+$): m/z=192 ($^{79}$Br), 194 ($^{81}$Br).

Example 2c

Dimethyl sulfate (0.53 g, 4.21 mmol) dissolved at 25° C. in 0.5 ml of N,N-dimethylformamide was added to a solution of 1.5 g (8.42 mmol) of 2-bromo-4-methylthiazole in 4.0 ml of N,N-dimethylformamide. After stirring at 25° C. for 3 hours, the solvent was removed in vacuo and the residue was codistilled three times with ethyl acetate to remove the last traces of DMF. The residue was recrystallized from isopropanol.

Yield of bis(2-bromo-3-methyl-4-methylthiazole) sulfate: 0.85 g (21%), white crystals M.p.: 149° C. $^1$H-NMR (400 MHz, MeOH-$d_3$): δ=2.65 (s, 3H, CH$_3$thiazole), 4.10 (s, 3H, CH$_3$), 7.98 (s,1H, thiazole). $^{13}$C-NMR (400 MHz, MeOH-$d_3$): δ=15.2, 40.2, 122.4, 146.8, 148.9. MS (ESI$^+$): m/z=192 ($^{79}$Br), 194 ($^{81}$Br).

Example 3

6.0 g (0.03 mol) of 2-bromo-3,4-dimethyl-1,3-thiazole dissolved in 25 ml of dichloroethane were added dropwise to a solution of 6.53 g (0.03 mol) of triethyloxonium tetrafluoroborate in 50 ml of dichloroethane such that a temperature of 20° C. was not exceeded. After addition was complete, the mixture was heated to reflux for 1 h, then cooled to room temperature and the product was crystallized by addition of 1,000 ml of methyl tert-butyl ether and recrystallized from isopropanol.

Yield of 2-bromo-3-ethyl-4,5-dimethylthiazole tetrafluoroborate: 9.5 g (98%), white crystals. M.p.: 235° C. (decomposition). $^1$H-NMR (400 MHz, CH$_3$CN-d$_3$): δ=1.40 (t, 3H, CH$_3$ CH$_2$CH$_3$), 2.45, 2.48 (2×s, 3H, CH$_3$, thiazole, 4.45 (q, 2H, CH$_2$CH$_3$). $^{13}$C-NMR (400 MHz, MeOH-d$_3$): δ=11.5, 11.73, 12.46, 49.04, 134.21, 139.54, 142.99. MS (GC/ESI$^+$): m/z=220 ($^{79}$Br), 222 ($^{81}$Br)

Example 4

12 g (0.06 mol) of 2-bromo-4,5,6,7-tetrahydrobenzothiazole dissolved in 25 ml of dichloroethane were added dropwise to a solution of 11.50 g (0.06 mol) of triethyloxonium tetrafluoroborate in 50 ml of dichloroethane such that a temperature of 20° C. was not exceeded. After addition was complete, the mixture was heated to reflux for 1 h, then cooled to room temperature and the product was crystallized by addition of 1,000 ml of methyl tert-butyl ether and recrystallized from isopropanol.

Yield of 2-bromo-3-ethyl-4, 5, 6, 7-tetrahydrobenzothiazole tetrafluoroborate: 16.0 g (86%), white crystals. M.p.: 208° C. $^1$H-NMR (400 MHz, CD$_3$CN): δ=1.40 (s, 3H, CH$_2$CH$_3$),1.75–2.00 (m, 4H, 2× CH$_2$), 2.80 (t, 2H, CH$_2$), 4.40 (q, 2H, CH$_2$CH$_3$). MS (GC/ESI$^+$): m/z= 246 ($^{79}$Br), 248 ($^{81}$Br)

Example 5

With the exclusion of atmospheric moisture, 2.84 g (15 mmol) of triethyloxonium tetrafluoroborate (Meerwein reagent) were dissolved at room temperature in 15 ml of dichloromethane. 2 g (15 mmol) of 2-chloro-4-methylthiazole were added thereto and the batch was boiled under reflux for 30 minutes. After cooling to room temperature and diluting with an excess of anhydrous ether, the residue was filtered off with suction and washed with diethyl ether.

2-Chloro-3-ethyl-4-methylthiazole tetrafluoroborate was obtained as a white powder in a yield of >90% of theory.

$^{13}$C-NMR (100 MHz, CD$_3$CN), δ=13.2, 14.5, 48.0, 120.3, 141.4, 146.7 $^1$H-NMR (400 MHz, CDCl$_3$), δ=1.42 (t,J=7.5 Hz, 3H), 2.55 (s, 3H), 4.42 (q,J=7.5, 2H), 7.68 (s,1H) Melting point: 203° C.

Example 6

With the exclusion of atmospheric moisture, 21.8 g (110 mmol) of triethyloxonium tetrafluoroborate (Meerwein's reagent) were suspended at room temperature in 150 ml of dichloroethane. 25 g (100 mmol) of 2-bromo-4-phenylthiazole were added thereto, and the mixture was then boiled under reflux for 30 min. After cooling to RT and diluting with an excess of anhydrous ether, the residue was filtered off with suction and washed with diethyl ether.

2-Bromo-3-methyl-4-phenylthiazole tetrafluoroborate was obtained in a yield of 59% of theory (22.0 g). Melting point: 111° C.

$^{13}$C-NMR (100 MHz, CDCl$_3$): δ=13.97, 49.53, 124.57, 127.06, 129.43, 130.12, 131.60, 144.31, 149.68. $^1$H-NMR (400 MHz, CDCl$_3$): δ=1.23–1.28 (t, 3H), 4.45–4.56 (d, 2H), 7.56–7.72 (m, 5H), 8.12 (s, 1H, thiazole). EI/MS: M$^+$=268 (Br$_{79}$), 270 (Br$_{81}$)

Example 7

25 g (140 mmol) of 2-bromo-4-methylthiazole were dissolved in 50 ml of dichloroethane and treated at room temperature with 8.85 g (70 mmol) of dimethyl sulfate. The mixture was then warmed to 50° C. for 1 h to complete the reaction. The solution was cooled to room temperature and treated with 300 ml of methyl tert-butyl ether. The crystals were filtered off with suction and then recrystallized from isopropanol.

2-Bromo-3,4-dimethylthiazolium methyl sulfate was obtained in a yield of 8.5 g (25.1% of theory). $^1$H-NMR (400 MHz, CDCl$_3$): 2.62 (s, 3H), 3.68 (s, 3H), 4.19 (s, 3H), 8.16 (s, 1H, thiazole). EI/MS (m/z): 279 (Br$_{79}$), 281 (Br$_{81}$).

Analogously to the Preparation Examples 1 to 7 and according to the general description of the preparation process according to the invention, it was also possible, for example, to prepare the compounds of the formula (I) listed in Table 1 below.

Starting Substances of the Formula (II)

Example II-A

At 10° C., 11.6 mol of hydrogen bromide were passed with the exclusion of moisture into a solution of 280 g (2.30 mol) of thiocyanatopropan-2-one in 4,500 ml of dichloromethane such that a temperature of 10° C. was not exceeded. Hydrogen bromide was generated from bromine and tetralin to the course of this reaction according to processes known from the literature. In a modification of the literature procedure, the addition of catalytic amounts of iron was dispensed with and the reaction temperature for the generation of hydrogen bromide was increased to 40° C. After the addition of the hydrogen bromide was complete (about 6 h), the mixture was stirred at room temperature for 12 h. The product obtained as the hydrobromide was filtered off with suction, washed with 1,500 ml of dichloromethane, and again suspended in 3,000 ml of dichloromethane. 2,500 ml of saturated sodium hydrogen carbonate solution were then added in a 20 liter glass reactor at 0° C. with vigorous mixing (9 600 min$^{-1}$) such that a temperature of 5° C. was not exceeded. The organic phase was separated off, dried over MgSO$_4$, and the solvent was distilled off at 30° C. and 50 mbar on a rotary evaporator. The residue that remained was then fractionally distilled.

Yield of 2-bromo-4-methylthiazole: 365 g (89%), colorless liquid B.p.: 51° C. (0.1 mbar) $^1$H-NMR (400 MHz, DMSO-d$_6$): δ=2.49 (s, 3H, CH$_3$), 6.85 (s,1H, thiazole). $^{13}$C-NMR (400 MHz, DMSO-d$_6$): δ=17.25, 117.21, 134.90, 153.46. MS (CI): (m/z)=M$^+$179, C$_4$H$_4$BrNS: 178.05.

Example II-B 31.66 g (870 mmol) of HCl gas were passed at 10° C. into a solution of 20 g (170 mmol) of thiocyanato-2-propanone in 500 ml of dichloro-methane. The mixture was then stirred at room temperature for 15 h. For the isolation of the product, the reaction mixture was treated with 1,500 ml of saturated sodium hydrogen carbonate solution and then extracted with dichloromethane. The combined organic phases were dried over magnesium sulfate and the solvent was distilled off on a rotary evaporator.

2-Chloro-4-methylthiazole was obtained in a yield of 12.9 g (55.6% of theory). $^{13}$C-NMR (100 MHz, CDCl$_3$), δ=16.9, 115.4, 151.4 $^1$H-NMR (400 MHz, CDCl$_3$), δ=2.43 (s, 3H), 6.85 (s, 1H, thiazole). Reference: Jurew et al.; *Zh. Obshch. Khim.*; 29; 1959; 2299; Engl. ed. p. 2263, Hantzsch; *Chem. Ber.*; 60; 1927; 2544.

Example II-C

HBr was passed at −30° C. for 20 min into a solution of 10.0 g (0.08 mol) of 3-thiocyanobutan-2-one in 300 ml of dichloromethane and the mixture was then warmed to 0° C. in the course of 10 min. In the course of this, HBr was continuously passed in and after 90 min the mixture was warmed to room temperature and the introduction of gas was ended in parallel. After the mixture had been stirred at room temperature for about 10 h, it was cooled to 0° C. and neutralized using a dilute aqueous sodium hydrogen carbonate solution. The organic phase was separated off, dried over MgSO$_4$, and the solvent was distilled off on a rotary evaporator.

Yield of 2-bromo-3,4-dimethyl-1,3-thiazole: 13.0 g (87.4%), yellow oil. MS (GC/EI$^+$): m/z=192 (M$^+$). $^1$H-NMR (400 MHz, CDCl$_3$): δ=2.36 (s, 3H, CH$_3$thiazole), 2.38 (s, 3H, CH$_3$ thiazole). $^{13}$C-NMR (400 MHz, CH$_3$CN-d$_3$): δ=11.25, 14.63, 130.23, 130.64, 148.74.

Example II-D

HBr was passed at 0° C. for 20 min into a solution of 12.02 g (77.41 mmol) of 2-thiocyanocyclohexanone (see, for example, Ali et al. 1981, *J. Chem. Res. Miniprint* 8, 2901–2927; Tanabe et al. 1994, *Chem. Left.* 12, 2275–2278) in 300 ml of dichloromethane and the mixture was then warmed to room temperature in the course of 10 min and at the same time HBr was passed in continuously. After 30 min, the introduction of gas was ended. After the mixture had been stirred overnight at room temperature, it was cooled to 0° C. and neutralized using a dilute aqueous sodium hydrogen carbonate solution. The organic phase was separated off, dried over MgSO$_4$ and the solvent is distilled off on a rotary evaporator.

Yield of 2-bromo-4,5,6,7-tetrahydrobenzothiazole: 12.0 g (65.4%), yellow oil. MS (GC/CI): m/z=218 (M$^+$) $^1$H-NMR (400 MHz, CDCl$_3$): δ=1.85 (m, 4H), 2.75 (m, 2H), 2.85 (m, 2H). $^{13}$C-NMR (400 MHz, CH$_3$CN-d$_3$): δ=22.75, 23.09, 23.40, 26.64, 132.34, 132.90, 150.94.

Analogously to the Preparation Examples 1 to 3 and according to the general description of the preparation process according to the invention, it was also possible, for example, to prepare the compounds of the formula (II) listed in Table 1 below.

Example II-E

With the exclusion of moisture, 100 g (0.56 mol) of 1-phenyl-2-thiocyanatoethanol were dissolved in 1,000 ml of dichloromethane and 228.27 g (2.82 mol) of hydrogen bromide were passed in at 10° C. in the course of 2 h. The mixture was then stirred at room temperature for 2 h. For work-up, the solution was treated with 2,000 ml of a saturated sodium hydrogen carbonate solution and then extracted with dichloromethane. The combined organic phases were dried over magnesium sulfate and the solvent was distilled off on a rotary evaporator.

2-Bromo-4-phenylthiazole was obtained in a yield of 84% of theory. $^{13}$C-NMR (100 MHz, CDCl$_3$): δ=116.48, 126.62, 129.07, 129.25, 133.63, 136.20, 156.20. $^1$H-NMR (400 MHz, CDCl$_3$): δ=7.43–7.52 (m, 4H), 7.84–7.93 (m, 2H)

Reference: Sharma, G. M. et al.; Tetrahedron; 15; 1961; 53–59.

TABLE 1

Examples of compounds of the formula (II)

(II)

where $R^4$ in each case represents bromine or chlorine.

| Ex. No. | $R^2$ | $R^3$ |
|---|---|---|
| II-D | $CH_3$ | $C_2H_5$ |
| II-E | | —$(CH_2)_3$— |
| II-F | | —$(CH_2)_4$— |
| II-G | | —$(CH_2)_5$— |
| II-H | $C_2H_5$ | $CH_3$ |
| II-I | $C_2H_5$ | $C_2H_5$ |
| II-J | | —$(CH_2)_3$— |
| II-K | | —$(CH_2)_4$— |
| II-L | | —$(CH_2)_5$— |
| II-N | n-$C_3H_7$ | H |
| II-O | n-$C_3H_7$ | $CH_3$ |
| II-P | n-$C_3H_7$ | $C_2H_5$ |
| II-Q | | —$(CH_2)_3$— |
| II-R | | —$(CH_2)_4$— |
| II-S | | —$(CH_2)_5$— |
| II-U | i-$C_3H_7$ | H |
| II-V | i-$C_3H_7$ | $CH_3$ |
| II-W | i-$C_3H_7$ | $C_2H_5$ |
| II-X | | —$(CH_2)_3$— |
| II-Y | | —$(CH_2)_4$— |
| II-Z | | —$(CH_2)_5$— |
| II-AB | n-$C_4H_9$ | H |
| II-AC | n-$C_4H_9$ | $CH_3$ |
| II-AD | n-$C_4H_9$ | $C_2H_5$ |
| II-AE | | —$(CH_2)_3$— |
| II-AF | | —$(CH_2)_4$— |
| II-AG | | —$(CH_2)_5$— |
| I-AI | s-$C_4H_9$ | H |
| II-AJ | s-$C_4H_9$ | $CH_3$ |
| II-AK | s-$C_4H_9$ | $C_2H_5$ |
| II-AL | | —$(CH_2)_3$— |
| II-AM | | —$(CH_2)_4$— |
| II-AN | | —$(CH_2)_5$ |
| II-AP | t-$C_4H_9$ | H |
| II-AQ | t-$C_4H_9$ | $CH_3$ |
| II-AR | t-$C_4H_9$ | $C_2H_5$ |
| II-AS | | —$(CH_2)_3$— |
| II-AT | | —$(CH_2)_4$— |
| II-AU | | —$(CH_2)_5$— |

Starting Substances of the Formula (V)

Example V-A

The 1-phenyl-2-thiocyanatoethanol needed for the preparation of 2-bromo-4-phenylthiazole (Example II-E) could be prepared as follows.

At room temperature, 200 g (1.01 mol) of bromoacetophenone were introduced into 1,000 ml of ethanol and then treated with 97.75 g (1.21 mol) of sodium thiocyanate. The mixture was stirred at room temperature for 3 h and the precipitate was filtered off. The mother solution was then concentrated on a rotary evaporator. The crude material had adequate purity for further reactions.

1-Phenyl-2-thiocyanatoethanol was obtained in a yield of 93% of theory. $^{13}$C-NMR (100 MHz, CDCl$_3$): δ=43.46, 121.26, 126.24, 128.85, 129.58, 134.31, 135.23, 191.21. $^1$H-NMR (400 MHz, CDCl$_3$): δ=4.75 (s, 2H), 7.24–7.93 (m, 5H).

Reference: J. Bariana et al.; J. Indian Chem. Soc.; 31; 1954; 848.

Use Examples

Reactivity Screening

The relative reactivity of the new peptide coupling reagents was determined in a reactivity screening. For this, 1.0 eq (54 mg, 0.2 mmol) of ClH$_2$N-MeIle-Bn was introduced into 10 ml of anhydrous dichloromethane and treated with 1.0 eq (49 mg, 0.2 mmol) of Boc-MeIle—OH (where in each case MeIle represents an N-methylisoleucine residue). 1.5 eq (0.3 mmol) of the coupling reagent to be tested (A to K, see FIG. 1) were then added to this solution at room temperature and after this was treated with 6 eq (1.2 mmol) of diisopropylethylamine. The reaction mixture was stirred at RT for 3 h and worked up on the micro scale for reaction control. For this, 200 microliters were withdrawn and treated with 200 microliters of a saturated NaHCO$_3$ solution. The organic phase was separated off and diluted with 1 ml of acetonitrile. For the determination of the starting material/product ratios, 5 microliters of this solution were measured by HPLC. The mobile phase used here was the system shown below: Waters Alliance 2690 system, UV detection, 214 nm; column: Waters Xterra C$_8$, 150×3.9 mm, flow: 1.2 ml/min; 0–13 min: 95% H$_2$O, 5% CH$_3$CN=>5% H$_2$O, 95% CH$_3$CN (0.1% TFA in solvent). In order to make a comparison with known coupling reagents, known coupling reagents (I, II, and III, see FIG. 1) were also tested using the described process. The degree of reaction was measured in relative units.

Figure 1:
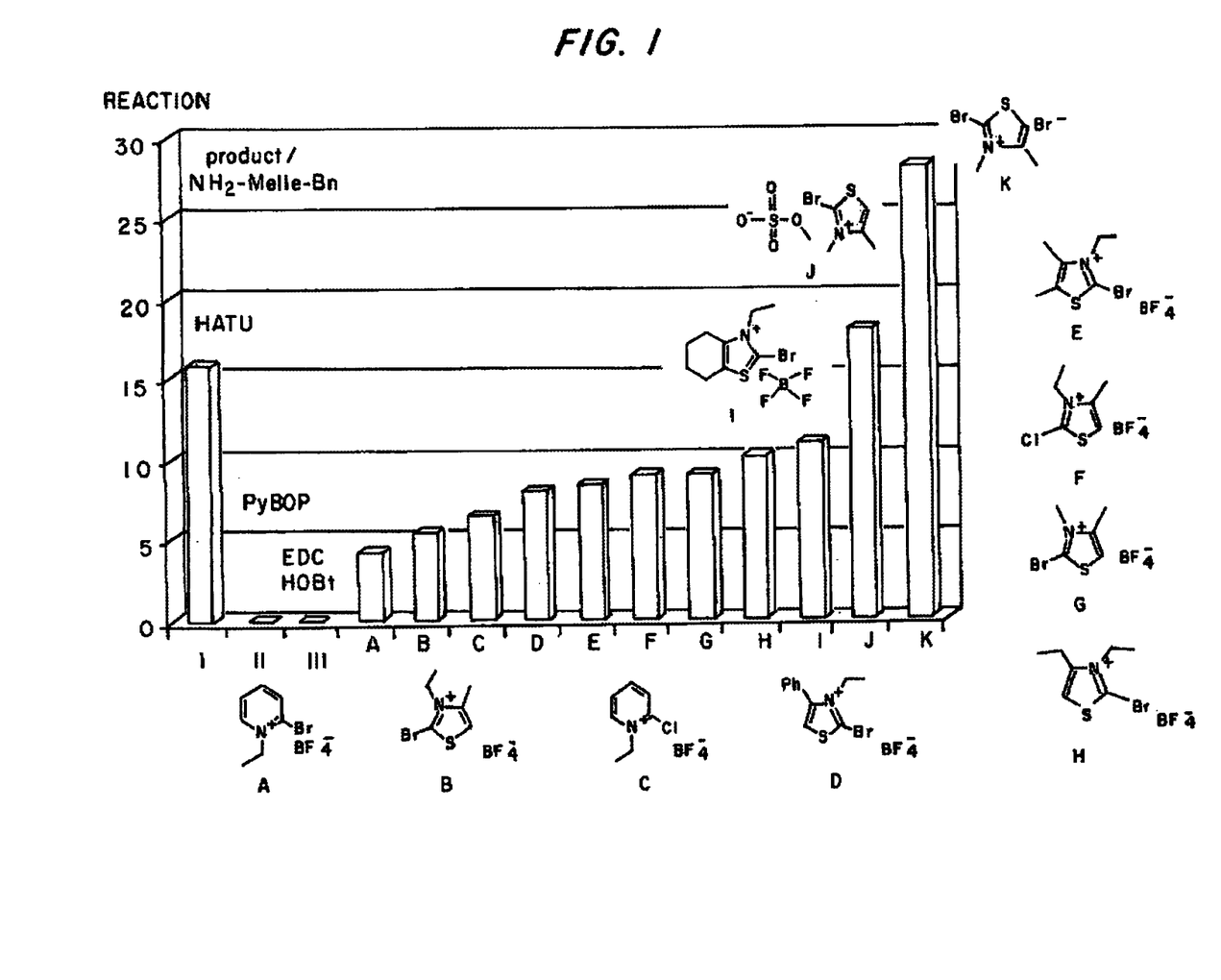
FIG. 1 shows the relative reactivities of compounds according to the invention when used as peptide coupling agents.

In FIG. 1, HATU represents O—(7-azabenzotriazol-1-yl)—N,N, N',N'-tetramethyluronium hexafluorophosphate; PyBOP represents 1-benzo-triazolyloxytripyrrolidinophosphonium hexafluorophosphate; EDC represents N'-(3-dimethylaminopropyl)-N-ethylcarbodiimide hydrochloride; and HOBt represents 1-hydroxy-1H-benzotriazole.

The reaction that was carried out can be described as follows:

-continued

In comparison with the known coupling reagents I, II, and III, the coupling reagents A to K exhibited very good reactivity.

What is claimed is:

1. A compound of the formula (I)

in which

R$^1$ represents methyl, ethyl, n-propyl, isopropyl, hydroxyl, methylsulfonyl, ethylsulfonyl, phenylsulfonyl, p-methylphenylsulfonyl, or benzyl that is optionally substituted by halogen, nitro, C$_1$–C$_4$-alkyl, trifluoromethyl, or C$_1$–C$_4$-alkoxy, R$^2$ and R$^3$ together represent —(CH$_2$)$_n$— that is optionally substituted by halogen, NO$_2$, carboxyl, carbonyl, C$_1$–C$_4$-alkyl, C$_1$–C$_4$-halogenoalkyl, C$_1$–C$_4$-alkoxy, or C$_1$–C$_4$-halogenoalkoxy or the optionally halogen-, NO$_2$—, C$_1$–C$_4$-alkyl-, C$_1$–C$_4$-halogenoalkyl-, C$_1$–C$_4$-alkoxy-, or C$_1$–C$_4$-halogenoalkoxy-substituted groups having the formulas where the arrows mark the points of linkage to the thiazole ring, and n represents 3, 4 or 5,

R$^4$ represents bromine or chlorine, and

X$^-$ represents chloride, bromide, iodide, hydrogen sulfate, ½ equivalent of sulfate, sulfate, hexachloroantimonate, methanesulfonate, trifluoromethanesulfonate, p-toluenesulfonate, tetrafluoroborate, tetraphenylborate, or hexafluorophosphate.

2. A compound of the formula (I) according to claim 1, wherein

R$^1$ represents methyl, ethyl, n-propyl, hydroxyl, methylsulfonyl, ethylsulfonyl, or benzyl that is optionally substituted by fluorine and/or chlorine, methyl, ethyl, n- or i-propyl, trifluoromethyl, methoxy, ethoxy, or n- or i-propoxy, R$^2$ and R$^3$ together represent —(CH$_2$)$_n$— substituted by fluorine and/or chlorine, methyl, ethyl, trifluoromethyl, methoxy, ethoxy, or carbonyl or the groups having the formulas and n represents 3 or 4, R$^4$ represents bromine, and X$^-$ represents bromide, ½ equivalent of sulfate, sulfate, SbCl$_6^-$, mesylate, triflate, tosylate, tetrafluoroborate, tetraphenylborate, or hexafluorophosphate.

3. A compound of the formula (I) according to claim 1, wherein

R$^1$ represents methyl, ethyl, methylsulfonyl, ethylsulfonyl, or benzyl that is optionally substituted by fluorine and/or chlorine,

R$^2$ and R$^3$ together represent —(CH$_2$)$_n$— that is optionally substituted by fluorine and/or chlorine, methyl, ethyl, or carbonyl, and X$^-$ represents bromide, ½ equivalent of sulfate, sulfate, or tetrafluoroborate.

4. A compound of the formula (I) according to claim 1, wherein

R$^4$ represents bromine.

5. A compound of the formula (I-2)

in which

R$^1$ represents methyl, ethyl, n-propyl, isopropyl, hydroxyl, methylsulfonyl, ethylsulfonyl, phenylsulfonyl, p-methylphenylsulfonyl, or benzyl that is optionally substituted by halogen, nitro, C$_1$–C$_4$-alkyl, or C$_1$–C$_4$-alkoxy, R$^2$ and R$^3$ together represent —(CH$_2$)$_n$— that is optionally substituted by halogen, NO$_2$, carboxyl, carbonyl, C$_1$–C$_4$-alkyl, C$_1$–C$_4$-halogenoalkyl, C$_1$–C$_4$-alkoxy, or C$_1$–C$_4$-halogenoalkoxy or the optionally halogen-, NO$_2$—, C$_1$–C$_4$-alkyl-, C$_1$–C$_4$-halogenoalkyl-, C$_1$–C$_4$-alkoxy-, or C$_1$–C$_4$-halogenoalkoxy-substituted groups having the formulas -continued where the arrows mark the points of linkage to the thiazole ring, and n represents 3, 4 or 5, $R^4$ represents bromine or chlorine, and $X''^-$ represents tetrafluoroborate, tetraphenylborate, or hexafluorophosphate.

* * * * *